United States Patent
Soars

(10) Patent No.: US 9,234,729 B2
(45) Date of Patent: Jan. 12, 2016

(54) INJECTION DART

(71) Applicant: Blair D. Soars, Williamsport, PA (US)

(72) Inventor: Blair D. Soars, Williamsport, PA (US)

(73) Assignee: PNEU-DART, INC., Williamsport, PA (US)

( * ) Notice: Subject to any disclaimer, the term of this patent is extended or adjusted under 35 U.S.C. 154(b) by 21 days.

(21) Appl. No.: 14/120,578

(22) Filed: Jun. 5, 2014

(65) Prior Publication Data

US 2015/0352285 A1 Dec. 10, 2015

(51) Int. Cl.
*F42B 12/54* (2006.01)
*A61M 5/20* (2006.01)
*A61M 5/168* (2006.01)

(52) U.S. Cl.
CPC ............ *F42B 12/54* (2013.01); *A61M 5/16813* (2013.01); *A61M 5/16881* (2013.01); *A61M 5/2033* (2013.01); *A61M 5/2053* (2013.01); *A61M 2005/2013* (2013.01)

(58) Field of Classification Search
CPC ........ F42B 6/003; F42B 12/362; F42B 12/40; F42B 12/54; A61M 2005/2013; A61M 2005/3128; A61M 5/16804; A61M 5/16877; A61M 5/16881; A61M 5/2033; A61M 5/16813; A61M 5/2053
USPC .......................................... 604/130; 102/512
See application file for complete search history.

(56) References Cited

U.S. PATENT DOCUMENTS

| 1,815,300 A | 7/1931 | Harris |
| 2,444,677 A | 7/1948 | Rosenbaum |
| 2,454,929 A | 11/1948 | Kempton |
| 2,854,925 A | 10/1958 | Crockford et al. |
| 2,936,788 A | 5/1960 | Dahl et al. |
| 3,022,785 A | 2/1962 | Crockford et al. |
| 3,207,157 A | 9/1965 | Murdoch |
| 3,209,695 A | 10/1965 | Crockford et al. |
| 3,266,806 A | 8/1966 | Warren et al. |
| 3,457,921 A | 7/1969 | Waldeisen |

(Continued)

FOREIGN PATENT DOCUMENTS

| WO | WO 8810129 | 12/1988 |
| WO | WO 9640351 | 12/1996 |

(Continued)

OTHER PUBLICATIONS

Ramiro Isaza—Remote Drug Delivery—Zoo Animal and Wildlife Immobilization and Anesthesia—(Portions of Chapter 4-207—Blackwell Publishing) (Also published online Apr. 14, 2008).

*Primary Examiner* — Bhisma Mehta
*Assistant Examiner* — James Ponton
(74) *Attorney, Agent, or Firm* — Thomas R. Shaffer, Esq.

(57) ABSTRACT

An improved injection dart is disclosed. A flow restrictor positioned at a forward end of a dart body is provided. The flow restrictor has a generally cylindrical restrictor body portion and a radially outward extending flange portion at a forward end thereof. The flange is securely held in position. The restrictor body also having a recess in a rearward end. The flange portion holds said restrictor in a position where an inner bore of a cannula is precisely aligned with the restrictor bore. The restrictor acts to diminish a variable flow rate so that all flow rates above a maximum flow rate are restricted to be less than the maximum flow rate. The flange also keeps a forward end of the flow channel bore open but allows for radially inward deformation of the restrictor at a rear end of said flow channel bore.

12 Claims, 3 Drawing Sheets

(56) References Cited

U.S. PATENT DOCUMENTS

| | | |
|---|---|---|
| 3,525,319 A | 8/1970 | Waldeisen |
| 3,833,019 A | 9/1974 | Diggs |
| 4,182,327 A * | 1/1980 | Haley ............... F42B 12/54 473/575 |
| 4,684,366 A | 8/1987 | Denny et al. |
| 4,735,612 A | 4/1988 | Chevalier |
| 2,923,243 A | 2/1990 | Crockford et al. |
| 5,209,265 A | 5/1993 | Taguri et al. |
| 5,266,325 A | 11/1993 | Kuzma et al. |
| 5,312,389 A | 5/1994 | Theewes et al. |
| 5,944,698 A | 8/1999 | Fischer et al. |
| 6,482,187 B1 | 11/2002 | Gibbs |
| 6,569,128 B1 | 5/2003 | Christensen et al. |
| 8,056,582 B2 | 11/2011 | DiPerna |
| 2012/0211946 A1* | 8/2012 | Halili ............... A61M 5/162 277/607 |
| 2013/0216483 A1 | 8/2013 | Weyer et al. |

FOREIGN PATENT DOCUMENTS

| | | |
|---|---|---|
| WO | WO 9706940 | 2/1997 |
| WO | WO 2004010073 | 1/2004 |

* cited by examiner

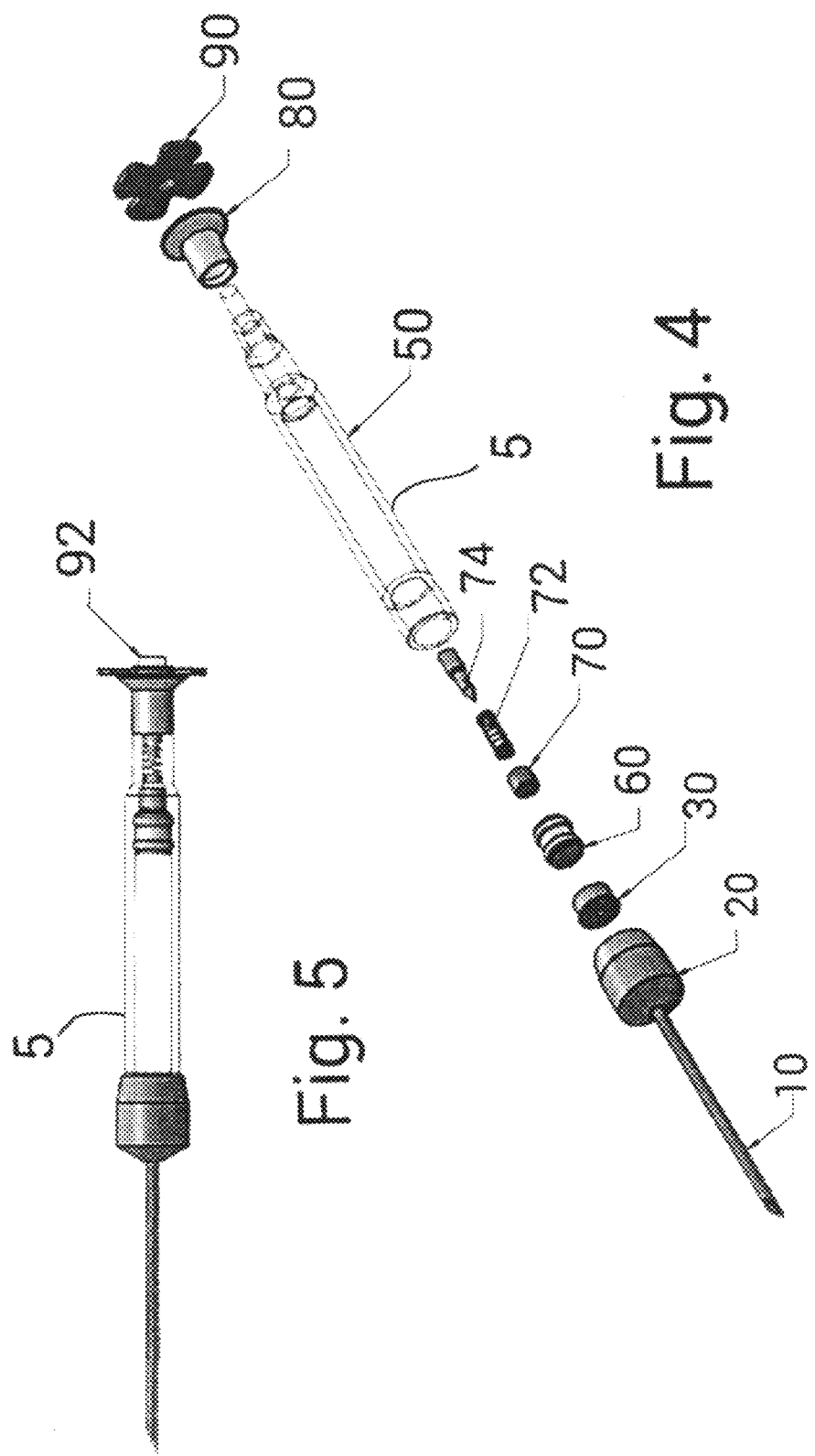

INJECTION DART

BACKGROUND OF THE INVENTION

1. Field of the Invention

The present invention relates to an improved injection dart. More specifically, it relates to an improved injection dart which employs a flow restrictor which limits and controls the rate of flow of an injection administered by the dart.

2. Description of the Prior Art

Dart-type projectiles carrying a self-contained actuating means which detonate upon rapid deceleration are generally well known in delivering drugs, medicines and the like to animals from a distance. Studies have concluded the rate of injection can and will disturb living tissue and in some instances result in partial injection due to the dart being propelled away from its intended target as a result of the speed of impact coupled with the rate of the injection rate. The use of hypodermic darts to administer anesthesia or other medications to animals is well known in the art. An early example is described and shown in Harris, U.S. Pat. No. 1,815,300. A number of injecting projectiles have been proposed by Crockford et al. including U.S. Pat. Nos. 2,854,925; 2,923,243; 3,022,785; and 3,209,695. Still other dart-like projectiles are described in Murdock, U.S. Pat. No. 3,207,157 and in Warren et al., U.S. Pat. No. 3,266,806. At the present time, injection darts are typically shot as projectiles from dart-projectors into the animal.

Publication No. WO 1988010129 A1, by Allan Kenneth Wallace teaches that a large number of drug reactions are due to the rate of injection, not the species of drug and that "[i]deally, the contents of a syringe need to be delivered over a number of minutes."

Fischer, U.S. Pat. No. 5,944,698, discloses an adjustable flow syringe. In one embodiment of the invention described in column 8, lines 24-36, Fischer teaches the provision of an adjustable flow syringe 90 which includes a porous inset 94 which is capable of performing the function of a flow restrictor means for restricting the flow rate of a fluid in the syringe such that any force within a range of forces that can be manually applied to plunger 14 delivers fluid at a substantially constant flow rate Rosenblum, U.S. Pat. No. 2,444,677, teaches a flow control device wherein fluid flowing through the casing must flow through the fixed orifice direct to the hollow shank or through the compensating orifice and ports into the hollow shank before it is discharged from the casing. The rubber ring deflects downstream in accordance with the pressure of the fluid to vary the capacity of the compensating orifice.

Kempton, U.S. Pat. No. 2,454,929, teaches a flow control which, as shown in FIG. 5, has a resilient annular member 11 which is deformed in the region of the orifice 17 when fluid under pressure is introduced in the bore 25 and is delivered through the bore 31 in the lower coupling member 26. The extent of deformation of the resilient annular member 11 depends upon the pressure drop across the orifice, the greater the pressure drop the greater the deformation. Such deformation causes a reduction in the diameter of the orifice.

Dahl et al., U.S. Pat. No. 2,936,788, teach a flow control system wherein disposed within the hollow interior of the housing 10 is a resilient, annular flow control washer 13 composed of rubber, chlorinated rubber, or similar elastic material. The flow control washer 13 is said to be effective to maintain a substantially constant flow over a wide range of pressure variations by its automatic reduction in the cross-sectional area of its orifice 13a upon increases in pressure thereon. Dahl et al. teach the provision of a flow control washer 13 which includes a frusto-conical face 13b.

Diggs, U.S. Pat. No. 3,833,019, teaches an irrigation system which employs a flow control device. A resilient compressible orifice member 34 is provided which has a conically shaped orifice 37 in its center. When the fitting is compressed, the compressible member to be deformed radially inwardly to decrease the size of the orifice 37 and thus restrict the rate of flow.

Taguri et al., U.S. Pat. No. 5,209,265, is yet another example of a flow control with a restrictor which includes an elastic valve 30 molded from a rubber or the like elastic material to have a small diameter section 31 and a large diameter section 32 with tapered periphery, as shown in FIG. 3. An aperture 33 is formed to extend through an axial center of the valve 30 for fluid communication between pipe 15 and passage 24. The valve 30 is capable of elastically deforming so as to vary the diameter of the aperture 33 in proportion to the pressure applied thereto, thereby allowing the water to flow through the aperture 33 at a controlled rate of keeping the flow volume at a constant level irrespective of the variation of pressure of the water being supplied.

Despite the many known examples of projectile darts and the many known methods of providing flow control, there remains a need for an improved injection dart which can address the difficult and complex problem of reliably and consistently injecting an animal with various medications at a rate which does not cause damage or injury to the tissue of the animal and does not cause the dart to eject from the animal's skin because of excessive backward pressure from a too rapid injection.

SUMMARY OF THE INVENTION

This invention relates to improvements in means for administering liquid drugs, medications and the like to animals and more particularly to a means for administering drugs, medicines and the like to an animal which are remotely situated or are unapproachable by a person desiring to administer the drugs, medicines and the like to such animal when using a medium to rapid injection rate dart for intramuscular or subcutaneous injections.

The present invention solves this problem by utilizing the general known principal of deforming an opening in an annular compressible rubber member to form a flow control function but provides a flow control member with unique geometries and features which provide reliable and consistent results in a very specialized environment where rapidly changing pressures may result because of the nature of the injection methods employed in injection darts.

It is the objective of this present invention to provide an improved means for administering drugs, medicines and the like to animals, by reducing the rate of injection for any medium to rapid rate injection dart manufactured to deploy drugs, medicines and the alike to an animal with minimum trauma to body tissues.

It is a further objective of this present invention whereby the improved means for administering drugs, medicines and the like is such that the device insures the dart is easily fillable or loadable with the drug or medicine to be administered.

Yet another objective of this present invention is to provide adaptability to a variety of nosecone and dart body designs at relatively low cost, simple construction, and which is easily operated.

In its simplest form, the present invention provides an improved injection dart of the type having a dart body, a ferrule at a forward end of said body to which a cannula is attached, a drug containment chamber located in said dart body, a plunger initially positioned at a rear end of said drug containment chamber, mechanical or chemical means to provide pressure to and exert force on a rear end of said plunger causing the plunger to move forwardly toward said cannula whereby a drug fluid within the drug containment chamber is discharged through said cannula at a variable flow rate, the improvement comprising: a flow restrictor positioned at a forward end of said dart body immediately juxtaposed against a rear end surface of said cannula, said flow restrictor having a generally cylindrical restrictor body portion, said flow restrictor having a radially outward extending flange portion at a forward end thereof, said flange securely held in position between a forward end of said dart body and said ferrule, said flow restrictor having a flow channel bore extending through a centerline of said cylindrical restrictor body from a forward end of said restrictor body to a rearward end thereof, said restrictor body also having a recess in a rearward end thereof said recess being symmetrically aligned along said centerline, whereby said flange portion holds said restrictor in a position where an inner bore of said cannula is precisely aligned with said restrictor bore and whereby said variable flow rate is altered such that all flow rates above a maximum flow rate are restricted to be less than said maximum flow rate.

Preferably, the holding of said flange in place also restricts radially inward deformation of the restrictor at a forward end of said flow channel bore keeping said forward end of said flow channel bore open but allowing for radially inward deformation of the restrictor at a rear end of said flow channel bore reducing the cross sectional area of said flow channel bore at such rear end thereby reducing the rate of flow which passes to the cannula.

Preferably, the holding of said flange in place also restricts radially inward deformation of the restrictor at a forward end of said flow channel bore keeping said forward end of said flow channel bore open but increasingly allowing for radially inward deformation of the restrictor at locations more distant from said forward end of said flow channel bore reducing the cross-sectional area of said flow channel bore at such locations thereby reducing the rate of flow which passes to the cannula.

Preferably, said recess in the rearward end of said restrictor body is frustoconical in configuration.

Preferably, said frustoconical recess has a diameter at said rearward end of said restrictor body portion which is about 0.6 times the diameter of said restrictor body leaving a flat rim portion around an outer circumference of the rear end of said restrictor body.

Preferably, said frustoconical recess has a diameter at a most forward end thereof of about 0.5 times the diameter of said restrictor body leaving a flat internal rim portion around an outer circumference of said flow channel bore.

Preferably, said frustoconical recess has a depth as measured from the rear end of said restrictor body to a most forward end thereof of between 0.25 times and 0.5 times the length of said flow restrictor.

Preferably, said variable flow rate is altered such that the flow rate is always above zero during discharge until all said drug fluid is discharged.

Preferably, said flow restrictor is formed from a compressible rubber material.

Preferably, said flow restrictor body portion has an outer diameter which is greater than an inner diameter of said drug containment chamber whereby even when said flow restrictor compressed to fit within said drug containment chamber said flow channel bore is not compressed beyond acceptable limits.

Preferably, said flow restrictor body portion has an outer diameter which is greater than an inner diameter of said drug containment chamber whereby even when said flow restrictor is compressed to fit within said drug containment chamber said flow channel bore has an inner diameter dimension of about 0.0575 inches.

Preferably, said flow restrictor body portion has an outer diameter which is greater than an inner diameter of said drug containment chamber whereby even when said flow restrictor is compressed to fit within said drug containment chamber said flow channel bore has an inner diameter dimension between 0.0560 inches and 0.0590 inches.

According to this invention, medium to rapid injection rate darts are facilitated through the means of a flow rate restrictor positioned within and at the end of the forward or anterior portion of the body between the end cap/nosecone of the dart.

BRIEF DESCRIPTION OF THE FIGURES

FIG. 4 is an exploded perspective view showing the various components of one form of injection dart including a flow restrictor according to the present invention.

FIG. 5 is a side elevational view of the injection dart of FIG. 4 in fully assembled form.

DETAILED DESCRIPTION OF THE PREFERRED EMBODIMENTS

Figure 1:
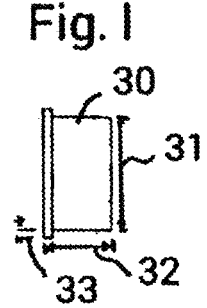
FIG. 1 is a side elevational view of the flow restrictor of the present invention.
Figure 2:
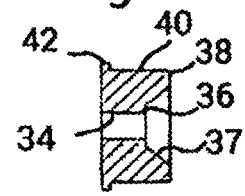
FIG. 2 is a cross-sectional view of the flow restrictor of the present invention.
Figure 6:
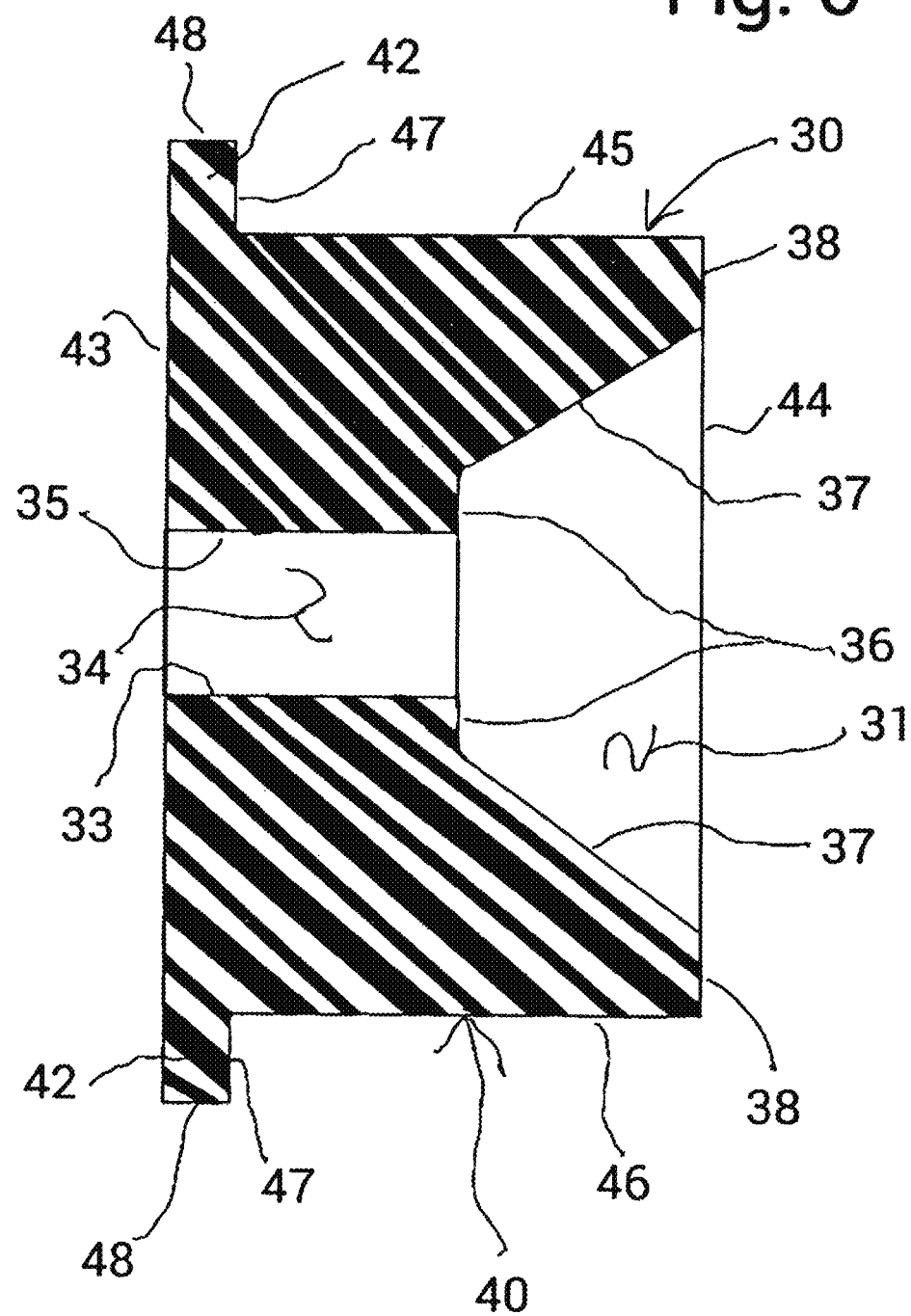
FIG. 6 is a cross-sectional view of the flow restrictor of the present invention showing additional details.

FIGS. 1, 2 and 6 show the details regarding the flow restrictor 30 of the present invention. An injection dart 5 into which the flow restrictor may be placed is shown in FIGS. 3, 4 and 5.

Figure 3:
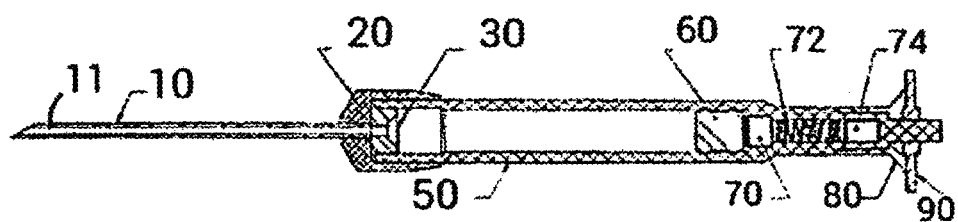
FIG. 3 is a cross-sectional view of the flow restrictor of the present invention as positioned within one form of an injection dart.

Referring to FIGS. 3, 4 and 5, the injection dart 5 (preferably approximately 4¾ inches long), includes a cannula (or injection needle) 10 at the dart's anterior or forward end. The cannula includes an inner bore 11 through which medications are injected into an animal. The cannula may also have an opening (not shown) along its cylindrical wall to allow for the passage of medications not only through the forward end of the inner bore 11 but also at a point along its length. The cannula 10 is aligned along and defines a centerline of the dart 5. The cannula 10 is firmly attached to the center of a ferrule 20. The ferrule 20 is a generally cylindrical cup shaped and has a closed forward end through with the cannula 10 extends and is preferably formed of aluminum or other light metal. The closed forward end may have a slightly sloping conical shape or may be flat. The conical shape, if utilized, allows for a more complete insertion of the entire exposed cannula 10 into the animal without interference from the ferrule. The rear portion of the ferrule is open and is sized to receive a forward end of a dart body 50. The dart body 50 may be formed from any suitable material such a polycarbonate, which is presently preferred, or from any other resin suitable composition or from aluminum or other metal, for example. As best shown in FIG. 3, the inside of the cup portion of the ferrule 20 has a flat inner surface against which a flat forward surface 43 (FIG. 6) of the flow restrictor 30 is juxtaposed.

Referring to FIGS. 3 and 6, the flow restrictor 30 has a flange portion 48 at a forward end and has a generally cylindrical body portion 40 at a rear end. The flow restrictor 30 has a length 33 (preferably approximately ⁵⁄₃₂ inch), has a body portion 40 with a diameter of 31 (preferably approximately ¹¹⁄₃₂ inch) and has a flange portion 42 which extends radially around the body portion 40 a distance 33 (preferably approximately ⅛₂ inch) and having a flange length or thickness (preferably approximately ⅛₂ inch). It will be understood that the flange portion 48 has two distinct and important functions. First, the flange portion 48 keeps the flow channel bore 34 which extends through a centerline of the flow restrictor body 40 precisely aligned with the inner bore 11 of the cannula 10. Second, because the flange portion 48 of the flow restrictor 30 is tightly held in position around the entire circumference at the forward end 43 of the flow restrictor 30, the flow channel bore 34 is deterred from inward deformation at such forward end 43 of the flow channel bore. The rear end of the bore 34 (that end closest to the internal annular flat surface portion 36) is not so deterred and when sufficient pressure is applied to the rear end 44 of the flow restrictor, the rear portion and to a lesser extent the intermediate portions of the flow channel bore 34 do expand radially inward causing a reduction in the flow rate to the cannula inner bore 11. A forward end of the dart body 50 is juxtaposed against the rear surface 47 of the flange 48. As mentioned, the forward surface 43 of the flange 48 is juxtaposed against a flat inner surface of the ferrule 20. The length of the flange portion 48 is not considered critical but should be long (thick) enough so that the high pressure forces to which it will be exposed will not cause the flange 48 to rip or tear away from the restrictor body portion 40. In this regard, upon activation of a rapid delivery dart, internal pressures encroach 2,000 PSI as the plunger is deployed and the pressure subsides. This is why the design of a suitable flow restrictor for this type of dart is so difficult and so necessary. The length of surface 47 or the flange 48 is preferably equal to or slightly less that the thickness of the sidewall portions of the dart body 50.

Referring to FIG. 6, the flow restrictor 30 has forward end 43 and rear end 44. The outer diameter of the body 40 (i.e. the distance between an upper end 45 and lower end 46 of the cylindrical body portion 40) is preferably greater than an inner diameter of said drug containment chamber. Even when said flow restrictor body 40 is compressed to fit within said drug containment chamber 50, said flow channel bore 34 is not compressed beyond acceptable limits. Preferably, even when said flow restrictor is compressed to fit within said drug containment chamber said flow channel bore 34 has an inner diameter dimension (i.e. the distance between upper surface 35 and lower surface 33) of about 0.0575 inches or between 0.0560 inches and 0.0590 inches.

The rear end 44 of the flow restrictor 30 has a recess 31 therein. Preferably, the recess 31 is frustoconical in configuration. Preferably, the frustoconical recess is provided such that a flat annular surface or rim portion 38 remains at the rear end 44 of the flow restrictor body 40 and such that a second inner flat annular surface or rim portion 36 remains at the rear opening of the flow channel bore 34. With this arrangement, the forces and areas of deformation under varying pressures are complex and depend on a number of variables, when the durometer or compressibility of the rubber material out of which the flow restrictor is made is held constant, it has been found that reliable, consistent and repeatable results can be achieved with the configuration of a flow restrictor as described herein. Clearly, the length of the flow channel bore 34 is critical. Since the forward end is essentially held open by the flange portion 48, if the length of the channel 34 is too short there will be insufficient flow reduction. If the length of the channel is too long, there is a possibility that it will completely close off under high pressure. Various shapes and configurations of the flow restrictor have been contemplated and tested but none has provided acceptable results for this type of use except where a forward flange is utilized in combination with a rear recess. The shape of the recess is not believed to be absolutely critical but it is highly recommended that the shape be symmetrical around a center line of the flow channel bore 34 and cannula 10. The recess might be dish shaped rather than purely frustoconical or may be frustoconical with slightly convex or concave surfaces. The preferred shape, however, is shown in FIG. 6. It is believed that the forward pressure of fluid against the flat rim portion 38, the second flat rim portion 36 and frustoconical surface 37 causes sufficient deformation at rear and mid-portions of the flow channel bore 34 to provide superior and repeatable results with multiple darts having the same flow channel bore 34 configuration. Preferably, said frustoconical recess has a diameter at said rearward end of said restrictor body portion which is about 0.6 times the diameter of said restrictor body leaving a flat rim portion 38 around an outer circumference of the rear end 44 of said restrictor body. Preferably, said frustoconical recess has a diameter at a most forward end thereof of about 0.5 times the diameter of said restrictor body leaving a flat internal rim portion 36 around an outer circumference of said flow channel bore 34.

Referring back to FIGS. 3, 4 and 5, the dart 5 also contains a P type plunger 60, a percussion cap 70, a P type spring 72, a firing pin 74, a P type slip fit tail 90 which is held in place by melted stem 92 (FIG. 5). As is well known, when this type of dart 5 is fired from a suitable dart projector, the cannula 10 is shot into the animal's body until the ferrule 20 hits the animals skin and immediately stops the forward momentum of the dart 5. However, the forward momentum of the firing pin 74 is sufficient to overcome the force of spring 72 causing the firing pin to strike the percussion cap 70 causing a controlled explosion within the dart body rearward the plunger 60. The percussion cap is typically a small cylinder of copper or brass with one closed end. Inside the closed end is a small amount of a shock-sensitive explosive material such as fulminate of mercury. The force of the explosion causes a rapid increase in pressure and causes the plunger 60 to move forwardly injecting the medication through the cannula into the animal. However, without the flow restrictor, damage to animal tissue may occur or the dart might fall out or be pushed out of the animal because of a too rapid injection flow rate. The flow restrictor 30 of the present invention may be utilized on both disposable darts or on darts which are designed to be reused.

It is to be understood that while certain forms of the present invention have been illustrated and described herein, the present invention is not to be limited to the specific forms or arrangements of parts described and shown.

I claim:

1. An improved injection dart of the type having a dart body, a ferrule at a forward end of said body to which a cannula is attached, a drug containment chamber located in said dart body, a plunger initially positioned at a rear end of said drug containment chamber, mechanical or chemical means to provide pressure to and exert force on a rear end of said plunger causing the plunger to move forwardly toward said cannula whereby a drug fluid within the drug containment chamber is discharged through an open end of said cannula at a variable flow rate, the improvement comprising:

a flow restrictor formed of a deformable material positioned at a forward end of said dart body immediately juxtaposed against a rear end surface of said cannula, said flow restrictor utilized to alter said variable flow rate only during times when said drug fluid within the drug containment chamber is being discharged through said cannula, said flow restrictor having a generally cylindrical restrictor body, said flow restrictor having a radially outwardly extending flange at a forward end thereof, said flange securely held in position between a forward end of said dart body and said ferrule, said flow restrictor having a flow channel bore extending through a centerline of said cylindrical restrictor body from a forward end of said restrictor body to a rearward end thereof, said restrictor body also having a recess in a rearward end thereof, said recess being symmetrically aligned along said centerline, whereby said flange holds said restrictor in a position where an inner bore of said cannula is precisely aligned with said restrictor bore and whereby said variable flow rate is altered by a radially inward deformation of the restrictor reducing a cross-sectional area of said flow channel bore thereby reducing said variable rate of flow which passes into the open end of the cannula such that all flow rates above a maximum flow rate are restricted to be less than said maximum flow rate.

2. An improved injection dart according to claim 1 whereby the holding of said flange in place also restricts radially inward deformation of the restrictor at a forward end of said flow channel bore keeping said forward end of said flow channel bore open but allowing for radially inward deformation of the restrictor at a rear end of said flow channel bore reducing the cross-sectional area of said flow channel bore at such rear end thereby reducing the rate of flow which passes into the open end of the cannula.

3. An improved injection dart according to claim 1 whereby the holding of said flange in place also restricts radially inward deformation of the restrictor at a forward end of said flow channel bore keeping said forward end of said flow channel bore open but increasingly allowing for radially inward deformation of the restrictor at a rear end of said flow channel bore located at the rearward end of said restrictor reducing the cross-sectional area of said flow channel bore at such rear end thereof thereby reducing the rate of flow which passes into the open end of the cannula.

4. An improved injection dart according to claim 1 wherein said restrictor body has an outer diameter, a length between said forward end and said rearward end and said recess in said rearward end of said restrictor body is frustoconical in configuration.

5. An improved injection dart according to claim 4 wherein said frustoconical recess has a diameter at said rearward end of said restrictor body which is about 0.6 times said outer diameter of said restrictor body leaving a flat rim portion around an outer circumference of the rear end of said restrictor body.

6. An improved injection dart according to claim 4 wherein said frustoconical recess has a diameter at a most forward end thereof of about 0.5 times said outer diameter of said restrictor body leaving a flat internal rim portion around an outer circumference of said flow channel bore.

7. An improved injection dart according to claim 4 wherein said frustoconical recess has a depth as measured from the rear end of said restrictor body to a most forward end thereof of between 0.25 times and 0.5 times said length of said flow restrictor.

8. An improved injection dart according to claim 1 wherein said variable flow rate is altered such that the flow rate is always above zero during discharge until all said drug fluid is discharged into the open end of the cannula.

9. An improved injection dart according to claim 1 wherein said flow restrictor is formed from a compressible rubber material.

10. An improved injection dart according to claim 1 wherein said flow restrictor body has an outer diameter which is greater than an inner diameter of said drug containment chamber whereby even when said flow restrictor is compressed to fit within said drug containment chamber said flow channel bore will not completely close off during times when said drug fluid is being discharged into the open end of said cannula.

11. An improved injection dart according to claim 1 wherein said flow restrictor body has an outer diameter which is greater than an inner diameter of said drug containment chamber whereby even when said flow restrictor is compressed to fit within said drug containment chamber said flow channel bore has an inner diameter dimension of about 0.0575 inches.

12. An improved injection dart according to claim 1 wherein said flow restrictor body has an outer diameter which is greater than an inner diameter of said drug containment chamber whereby even when said flow restrictor is compressed to fit within said drug containment chamber said flow channel bore has an inner diameter dimension between 0.0560 inches and 0.0590 inches.

* * * * *